United States Patent
Corzani

(10) Patent No.: US 6,403,113 B1
(45) Date of Patent: Jun. 11, 2002

(54) ANTI-MICROBIC AGENT

(75) Inventor: Italo Corzani, Chieti (IT)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/463,152
(22) PCT Filed: Jul. 16, 1998
(86) PCT No.: PCT/US98/14690
§ 371 (c)(1), (2), (4) Date: Jan. 19, 2000
(87) PCT Pub. No.: WO99/03344
PCT Pub. Date: Jan. 28, 1999

(30) Foreign Application Priority Data

Jul. 17, 1997 (EP) .............................. 97112206

(51) Int. Cl.[7] .............................................. A01N 25/10
(52) U.S. Cl. .................... 424/404; 424/78.18; 424/405; 424/407; 424/411; 424/414; 424/430; 424/431; 523/111; 523/122
(58) Field of Search ................................ 424/404, 405, 424/407, 409, 411, 414, 430, 431, 78.18; 523/111, 122

(56) References Cited

U.S. PATENT DOCUMENTS

| | | | |
|---|---|---|---|
| 5,320,830 A | 6/1994 | Lukacovic et al. | ........... 424/52 |
| 5,534,265 A | 7/1996 | Fowler et al. | .............. 424/489 |

Primary Examiner—Neil S. Levy
(74) Attorney, Agent, or Firm—Kirsten K. Stone; Matthew P. Fitzpatrick; Steven W. Miller

(57) ABSTRACT

Anti-microbic copolymers and derivatives thereof are used in methods for controlling odor in hygienic articles. The copolymers comprise at least two different ethylenically unsaturated monomers.

18 Claims, 5 Drawing Sheets

PLATE CONTAMINATED WITH:
CANDIDA ALBICONS
OR, ASPERGILLUS NIGER

SUBOURAUD DESTROSE AGAR

TEST PLATE CONTAMINATED WITH ONE OF THE THREE TEST COPOLYMERS

ESCHERICHIA COLI

STAPHYLOCOCCUS AUREUS

STREPTOCOCCUS

PSEUDOMONAS AERUGINOSA

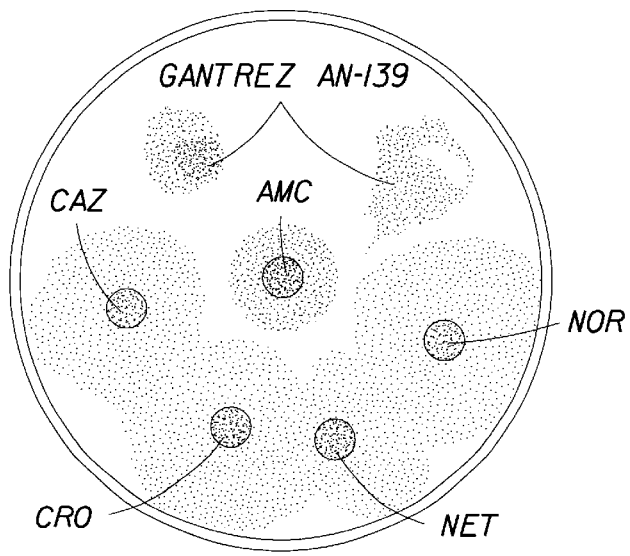
PROTEUS VULGARIS   Fig. 1E
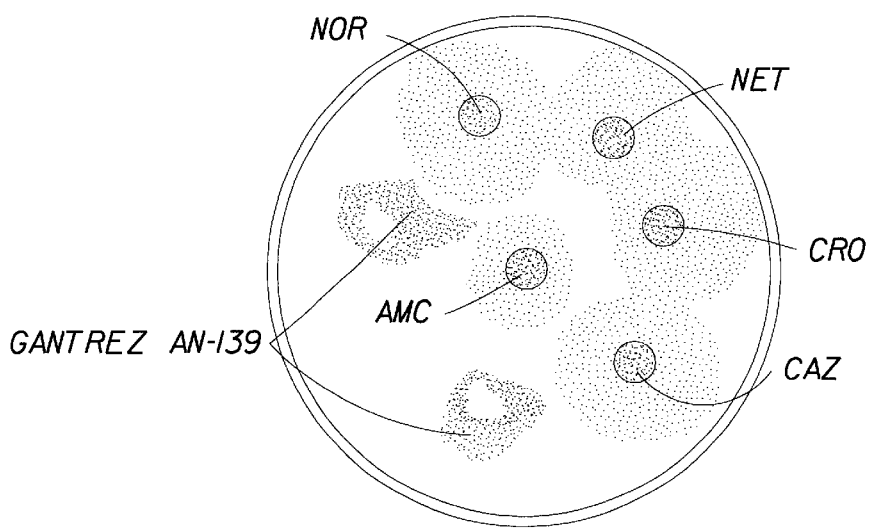
ASPERGILLUS NIGER   Fig. 1F

PLATE CONTAMINATED WITH:
CANDIDA ALBICONS
OR, ASPERGILLUS NIGER

SUBOURAUD DESTROSE AGAR

TEST PLATE CONTAMINATED
WITH ONE OF THE THREE TEST
COPOLYMERS

ANTI-MICROBIC AGENT

This application is a 371 of PCT/US98/14690 filed Jul. 16, 1998.

This invention relates to the use of certain copolymers and derivatives thereof as anti-microbic agents.

Many applications exist where it is necessary or at the very least an advantage for agents to be present which demonstrate anti-bacterial, anti-mycotic activity or both, resulting in the control of bacterial and/or fungal growth. For example, an apparatus or article as a whole or in part may have the property of suppressing bacterial and fungal growth. Control of bacterial and/or fungal growth may be through the prevention or inhibition of the growth of such microbes.

U.S. Pat. No. 4,248,685 discloses random interpolymers which can be used as superabsorbent materials prepared by the polymerization in aqueous medium of (A) a mixture of monomers comprising (1) up to about 90% by weight of an ester of an a, β-olefinically unsaturated carboxylic acid and a monohydric or polyhydric alcohol having a terminal quaternary ammonium group and (2) at least one a, β-olefinically unsaturated comonomer, in the presence of (B) a crosslinking agent comprising a difunctional monomer derived from an a, β-olefinically unsaturated carboxylic acid, which is bacteriostatic and is capable of adsorbing large multiples of its own weight of water.

WO92/09289 teaches an improved method for treating diaper rash of neonates, infants, children and incontinent adults which entails applying to the site of diaper rash a composition comprising 15–40% of a copolymer or a derivative thereof, of a lower alkyl vinyl ether and maleic acid dispersed in a semisolid ointment base.

U.S. Pat. No. 4,381,784 discloses an absorbent device designed to absorb blood or blood-like fluids such as a sanitary napkin which is combined with a blood gelling agent which includes, amongst others, maleic anhydride copolymers.

It has now been found that certain copolymers can be used to control or prevent the growth of microbic agents such as bacteria and fungus. It has further been found that certain derivatives of these copolymers also have anti-bacterial and anti-mycotic properties. The finding that the copolymers of the invention and derivatives thereof which are preferably of high molecular weight can be used as anti-bacterial and/or anti-mycotic agents provides many advantages over anti-microbic agents of the prior art, in particular, due to the large molecular weight and polymeric character of the anti-microbic agents of the invention. Furthermore, the copolymers or derivatives per se or blends of said copolymers or derivatives can be formed into articles or incorporated into articles in the form of films, fibers, adhesives etc.. The copolymers of the invention have a low toxicity due to their high molecular weight and possess intrinsic anti-bacterial and anti-mycotic activity. The use of the copolymers of the invention in the manufacture of certain articles may avoid the need to incorporate a separate constituent part to impart anti-microbic properties into an article. Moreover many anti-microbial substances available in the prior art are unsuitable for use in contact with humans and animals due to their toxicity. This applies both to non-polymeric and polymeric substances. Most of the polymers already known to possess anti-bacterial activity, show an inverse proportionality between molecular weight (and so toxicity) and anti-bacterial activity. Hence while such substances possess high biological activity at low molecular weights (insufficiently high in particular to avoid significant toxic effects on humans and animals), their activity is rapidly lost or become too low, when the molecular weight increases towards the range of real polymers and consequently, also their toxicity for superior organisms decreases. Hence, there is a need to combine suitable polymeric properties required for effective formation of a part or the whole of an article with inherent anti-bacterial and/or anti-mycotic properties to provide an article having the necessary physical parameters but demonstrating anti-microbic activity also.

The invention relates to the use of a copolymer comprising at least two different ethylenically unsaturated monomers A and B or a derivative of said copolymer as an anti-bacterial, an anti-mycotic agent or both wherein monomer A is according to the formula:

$$R^1\!-\!CH\!=\!CH\!-\!R^2$$

and wherein monomer B is according to the formula:

$$R^3\!-\!C(R^1)\!=\!C(R^2)\!-\!R^4$$

wherein $R^1$ and $R^2$ are independently selected from hydrogen; hydroxy; halogen; carboxy; sulfo; phenyl; phenoxy; $C_{1-6}$ alkyl, $C_{1-6}$ alkoxy, $C_{1-6}$ aminoalkyl, $C_{1-6}$ haloalkyl wherein the halogen is selected from chlorine, bromine, iodine, and fluorine, preferably chlorine; $C_{1-6}$ alkylphenyl; amino and $C_{1-6}$ alkylamino, $R^3$ is an acidic group or a derivative thereof and $R^4$ is a group selected from any of the definitions given hereinbefore for $R^1$, $R^2$ or $R^3$, with the proviso that neither monomer A nor monomer B is an ester having a quaternary ammonium compound.

According to an embodiment of the invention, monomer A is according to the formula:

$$R^1\!-\!CH\!=\!CH\!-\!O\!-\!R^2$$

wherein $R^1$ is as defined hereinbefore and $R^2$ is selected from phenyl, $C_{1-6}$ alkyl, $C_{1-6}$ aminoalkyl, $C_{1-6}$ haloalkyl, $C_{1-6}$ alkylphenyl, and $C_{1-6}$ alkylamino. More preferably, $R^1$ is hydrogen and $R^2$ is $C_{1-6}$ alkyl.

According to a further embodiment, monomer B is a dibasic acid according to the formula:

$$R^3\!-\!C(R^1)\!=\!C(R^2)\!-\!R^4$$

in which $R^3$ and $R^4$ are both carboxyl and $R^1$ and $R^2$ are as defined hereinbefore, and according to an embodiment of the invention both $R^1$ and $R^2$ are hydrogen.

It is preferred that when the copolymer of the invention is comprised of more than two monomers, monomers A and B form at least 90% in moles of the total copolymer. It is further preferred that the molar ratio of monomers A and B is from 60:40 to 40:60, it being most preferred that the copolymer comprises a substantially equal molar content of monomers A and B.

According to a further embodiment, the copolymer is substantially an alternate copolymer where monomers A and B alternate according to the structure:

$$-\!A\!-\!B\!-\!A\!-\!B\!-\!A\!-\!B\!-\!A\!-\!B\!-$$

The copolymer of the invention may further comprise monomers C, which may form up to 10% in moles of the total copolymer and individually, may form up to 5% in moles of the total monomer. The additional monomers may be any ethylenically unsaturated monomer provided that they are polymerisable with monomers A and B. The additional monomer may occupy any position in the polymer chain, but preferably the additional monomers are homogenously dispersed, more preferably according to one of the following structure:

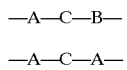

or

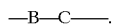

According to a further embodiment of the invention, $R^3$ in monomer B is a sulfo or carboxy group or a derivative thereof and $R^4$ is an acidic group or a derivative thereof, preferably also a sulfo or carboxy group or a derivative thereof. When two contiguous carboxy groups are present in the copolymer of the invention, the cyclic anhydride derivative may be also usefully employed.

The acidic groups of monomers A and B can be defined as meaning that all the acidic groups of the monomers may be present either as free acidic groups or as corresponding anhydrides or alternatively, as derivatives or as derivatives that can be formed from said free acid groups or corresponding anhydrides, for example, esters, salts, amino-ammonium salts, amides, imides, complexes with inorganic and organic compounds etc, by reaction under suitable conditions conventionally used.

Specific examples of monomer A include, but are not limited to: alkyl vinyl ethers selected from vinyl methyl ether, vinyl ethyl ether, vinyl propyl ether, vinyl isopropyl ether, vinyl n-butyl ether, vinyl isobutyl ether, vinyl n-amyl ether, vinyl n-hexyl ether; and alkoxy alkyl vinyl ethers selected from methoxyethyl vinyl ether, ethoxyethyl vinyl ether, propoxyethyl vinyl ether, butoxyethyl vinyl ether, methoxyethoxyethyl vinyl ether, ethoxyethoxyethyl vinyl ether, butoxyethoxyethyl vinyl ether.

The most preferred copolymer according to the invention is one in which monomer A is methyl vinyl ether and monomer B is maleic acid or a derivative thereof, more preferably, monomer B is a cyclic anhydride of maleic acid (maleic anhydride).

According to an embodiment of the invention, the molecular weight of Monomer A is about 1000 Daltons or less, preferably, 600 Daltons or less and more preferably, 300 Daltons or less.

The copolymers of the invention and derivatives thereof have molecular weights preferably greater than about 10,000 Daltons, preferably in a range of from about 10,000 to about 100,000 Daltons, optionally in a range of from about 20,000 to 80,000 or from 40,000 to 60,000 Daltons.

Copolymers of methyl vinyl ether and maleic acid/maleic anhydride are commercially available and sold under the tradename GANTREZ®, available from International Speciality Products (ISP), New Jersey, U.S.A. For example these copolymers include, Gantrez® AN-119 copolymer (molecular weight of approximately 20,000), Gantrez® AN-139 copolymer (molecular weight of approximately 41,000), Gantrez® AN-149 copolymer (molecular weight of approximately 50,000), Gantrez® AN-169 copolymer (molecular weight of approximately 67,000), Gantrez® AN-179 copolymer (molecular weight of approximately 80,000), Gantrez® MS-955 (mixed calcium and sodium salt blend of the methyl vinyl ether/maleic acid copolymer, in which the proportion of Ca:Na is about 5–6:1 and the molecular weight is about 65,000–70,000), Gantrez® S-97 (copolymer has intact acid groups), Gantrez® ES-353 (monoisopropyl ester derivative of the copolymer) and Gantrez® ES-435 and ES-425 (monobutyl ester derivatives of the copolymer).

Therefore, the most preferred alternate copolymers of the invention, have the following formulae:
-methyl vinyl ether and maleic anhydride-

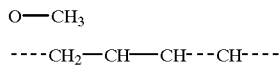

or
-methyl vinyl ether and maleic acid-

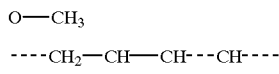

or derivatives of such compounds.

The derivatives of the copolymers of the invention, in particular methyl vinyl ether and maleic anhydride, which can be most suitably used include any derivative which has the required anti-bacterial and/or anti-mycotic properties. Preferably, the derivatives of the copolymers are selected from free acidic forms of said copolymers; esterified derivatives of said copolymers and salts thereof; amide derivatives or imide derivatives of the copolymers or salts thereof, or mixed amide/imide derivatives of said copolymers or salts thereof; complexes of said copolymers and iodine formed, for example, when iodine is added to an aqueous solution of the copolymer; complexes of said copolymers and polyvinyl pyrrolidone; and derivatives obtained from the reaction of said copolymers with polyhydroxy compounds and polyamines, in particular, derivatives obtained from partial or complete neutralization of the acidic groups with glycerin, glycols, polyglycols, polyvinyl alcohol, pentaerythritol, sorbitol, diols and polydiols and the like.

The free acid derivative of the copolymer of the invention, may be formed when the copolymer is dissolved in water to cause the anhydride linkage to be cleaved to form the highly polar, polymeric free acid. The corresponding partial ester is formed if the copolymer is dissolved in alcohol, for example, mono-hydroxy acyclic, saturated cyclic, aromatic, and terpenic alcohols or phenols. Both these derivatives of the preferred methyl vinyl ether/maleic anhydride copolymer of the invention are commercially available from ISP, New Jersey under the tradenames Gantrez® S and Gantrez® ES series (registered trademarks), respectively, and have the formulae:

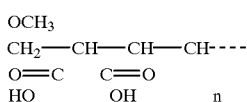

free acid derivative of the poly(methyl vinyl ether/maleic anhydride) copolymer obtained by dissolving Gantrez AN in water, which reacts with the anhydride groups to form the acid.

and

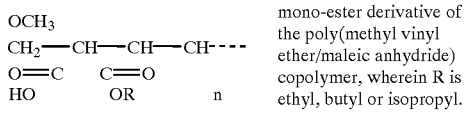

mono-ester derivative of the poly(methyl vinyl ether/maleic anhydride) copolymer, wherein R is ethyl, butyl or isopropyl.

In each case n is determined by the required molecular weight of the polymer.

The copolymers may also be used as derived salts, in particular, salts derived from alkaline metals selected from lithium, sodium, potassium, rubidium, caesium and francium, alkaline earth metals selected from magnesium, calcium, strontium, barium and radium or salts derived from aluminium, iron, zinc, silver, copper and mercury. Furthermore, these derivatives may be salified with different metals on the various acidic groups of the same molecule.

Esterification can also occur when anhydride copolymers of the invention are added directly to a nonionic surfactant or to an aqueous solution thereof.

When anhydride derivatives of the copolymers of the invention, for example, poly(methyl vinyl ether/maleic anhydride) copolymer, are reacted with ammonia or amines, the anhydride linkage is cleaved to form salts or half-amide salts. For example, anhydrous ammonia can be bubbled through a benzene slurry of the copolymer to form a half amide which may then be converted to the imide by heating with acetic anhydride. Substituted amides may be prepared by reacting a copolymer of the invention with primary or secondary amines under similar conditions to those described for the preparation of the half-amide of the copolymer.

Complexes of the copolymer of the invention can be formed with polyhydroxy compounds and polyamines. In addition, complexes can be formed with polyvinylpyrrolidone (PVP), as well as with gelatin, iodine, ferric, mercuric and lead salts, amongst others.

Polyvinylpyrrolidone/poly(methyl vinyl ether/maleic anhydride) complexes are particularly preferred. PVP complexes with the copolymer of the invention, or alternatively with the half-amide or partial ester of the copolymer, can be formed when PVP and the copolymer of the invention or the amide or ester derivative thereof are mixed at room temperature in an aqueous solution or an organic-solvent solution below pH5. The reaction conditions are preferably in proportions ranging from 4:1 to 1:4.

The copolymers of the invention are commercially available and produced by conventional polymerization methods, which will depend on the properties of the specific monomers used. Hence, any known polymerization method suitable for polymerization of ethylenically unsaturated monomers may be used, for example, bulk polymerization, solution polymerization, emulsion polymerization, suspension polymerization etc.. Copolymers of alkyl vinyl ethers, for example, methyl vinyl ether and maleic anhydride, can be prepared in accordance with the polymerization method described in GB patent no. 1200472.

The copolymers of the invention or derivatives thereof not only exhibit anti-bacterial and/or anti-mycotic activity, but beneficially have the typical properties of thermoplastic polymers with a high molecular weight. The copolymers, therefore, can be extruded and formed into different geometrical forms when in the molten state by conventional means.

Copolymers and derivatives thereof according to the invention can be used as blends with suitable additives, such as plasticizers, which are well known in the field of thermoplastic polymers. For example, suitable plasticizers include glycerol, dimethyl phthalate, diethyl phthalate, diethylene glycol, triethylene glycol, sorbitol, tricresyl phosphate, dimethyl sebacate and ethyl glycolate. Hence, the soluble copolymers and derivatives according to the invention may be processed into articles such as films, by deposits from solutions and in particular from aqueous solutions. Additionally, copolymers of the invention or derivatives thereof in either solution or film form, are compatible with a wide variety of water-soluble resins and gums and with polyvinyl chloride, polyvinyl acetate etc. and copolymers thereof. Hydrolyzed poly(methyl vinyl ether/maleic anhydride) copolymer is compatible in aqueous solution with a number of emulsifiers and wetting agents, preferably, for example when equal volumes of a 2.5% emulsifier solution and a 5% copolymer solution are mixed.

Poly(methyl vinyl ether/maleic anhydride) copolymers and other copolymers according the invention are soluble in water and polar solvents, such as, alcohols, glycols, etc. from which solutions, films and coatings can be formed depending on the intended application of the copolymer. Hence, the copolymers or derivatives thereof can be formed into films, fibers, adhesives, protective, colloids, thickeners, gelling agents, etc. or in fact any use or application for which the copolymers or their derivatives are suitable so that by such use, they impart anti-bacterial and/or bacteriostatic activity and/or anti-mycotic activity. The Gantrez® AN copolymer half amide derivative, for example, is soluble in water and is particularly effective, for example, as a thickener or as a colloidal preparation having adhesive properties. Some of the derivatives of the copolymers of the invention may not be soluble in water but are swellable with water. Such derivatives can be used to thicken water based liquids to form gels etc. For example, the crosslinked derivatives of the copolymers of methyl vinyl ether/maleic anhydride may be used in this way as an absorbent material, for example, in hygienic articles. Hence, these polymers have a dual function in that they absorb liquid and prevent microbial growth, additionally inhibiting the formation of unpleasant odours.

Certain of the copolymers, derivatives or complexes formed with the copolymers of the invention may be insoluble in water and, therefore, have uses as protective coatings, binding agents or as permanent finishes to surfaces to which they are applied, for example, the copolymer/PVP complex.

The copolymers of the invention and derivatives thereof have particular advantages when used in hygienic articles, and they can be introduced as solid components, powders, solutions, gels etc. by conventionally available techniques. It is particularly preferred that the polymeric anti-bacterial and/or anti-mycotic compounds of the invention are used to serve further functions in the hygienic article or in other applications, for example, it is preferred that they form part or the whole of an article, and may be in the form of films, fibers, adhesives, absorbent materials etc.. Use in this way of the copolymers or their derivatives according to the invention avoids the need to use multiple components to provide different properties.

Examples of uses of the copolymers of the invention and derivatives thereof include their incorporation into the woven or non-woven components of hygienic articles, preferably in particular form, such as, paper products, absorbent articles, such as, disposable absorbent articles, for example, sanitary towels, tampons, pantiliners, diapers, training pants, incontinence pads and the like. Other uses include use as an adhesive or as a coating on the surface of an article or apparatus where it is beneficial to prevent the growth of bacteria or fungus or, where, for example, such articles or apparatus contact a human or animal body and so it is important to prevent the spread of infection, for example, medical equipment, dressings for wounds, pharmaceutical products, veterinary products etc. The copolymers and derivatives thereof may also be used, for example, in cosmetics, detergents and pharmaceuticals to prevent contamination of such products through growth of bacteria and/or fungus and to maintain sterility. Additionally, the polymeric compounds of the invention may be used in paints, varnishes, sealants etc. to prevent the growth of mould either when the product is being stored or after use once the product has been applied to a surface. The copolymers of the invention or derivatives thereof may also be added to paper products, textiles, leather goods etc. to prevent spoiling of such articles by contamination by bacteria or fungus.

One particularly preferred application of the copolymers and derivatives thereof is as odour control agents, for example, in any hygienic article or anti-odour product used to control or suppress odours, for example, body odours which may be derived from excreted body fluids where bacteria and/or mycotic flora either cause or enhance unpleasant odours. The polymeric compounds according to the invention have been shown to be effective at controlling or preventing the occurrence of such odours when used to form hygienic articles or when incorporated into an article as a portion which will contact an area of a body, for example, which is prone to the formation of body odours or when added to a cosmetic product.

The copolymers of the invention and derivatives thereof can also be used to provide preservative systems. Examples of suitable uses of the copolymers as preservative systems include use in water based adhesive compositions such as those described in WO94/26834, which comprises a blend of adhesive polymers in an aqueous system, the blend of polymers comprising 20–60 wt % of an acrylic polymer having a polarity balance expressed as water-absorption according to DIN 53495 of 3–20%, and 40–80 wt % of a compatible tackifying resin having a degree of hydrophobicity measured as the contact angle between a dried film of the resin and a drop of distilled water of not less than 60deg. WO94/26834 is incorporated herein by reference. Use of the copolymers or their derivatives in this way prevents the formation of mould during storage of a composition leading to biological degradation of the compositions.

The copolymers and derivatives according to the invention can be used in any application where the control or prevention of growth of bacteria and/or fungus or the suppression of such growth is required. The copolymers of the invention can be used together with any additional components, for example, additional anti-bacterial/anti-mycotic agents, anti-odour agents, perfumes etc. as required, as long as the additional components do not affect the anti-bacterial or anti-mycotic properties of the polymers of the invention.

The invention will now be illustrated further with reference to the following Examples and Figures, which are not intended to be limiting.

FIG. 1E shows a plan view of a culture plate after incubation showing the reaction of the applied reference antibiotics and the applied copolymer Gantrez AN-139 to *Proteus Vulgaris* bacteria.

FIG. 1F shows a plan view of culture plate after incubation showing the reaction of the applied reference antibiotics and the applied copolymer Gantrez AN-139 to *Aspergillus Niger* fugus.

EXAMPLE 1

Gantrez AN-139 (poly(methyl vinyl ether/maleic anhydride)) and Comparative Results with Reference Antibiotics.

The results show that Gantrez AN-139 has anti-bacterial properties comparable with results seen for reference antibiotics. The part of the test surface covered with Gantrez AN-139 appears completely sterile.

The method used for the in vitro calculation of bacterial sensitivity of various test compounds is based on the evidence of the inhibitory activity of the test compound on microbic development and it is referred to as the diffusion method. This procedure is used also for comparative antibiotics and is identical to the procedure used for Gantrez AN-139. The results, therefore, provide a direct comparison.

Figure 1A:
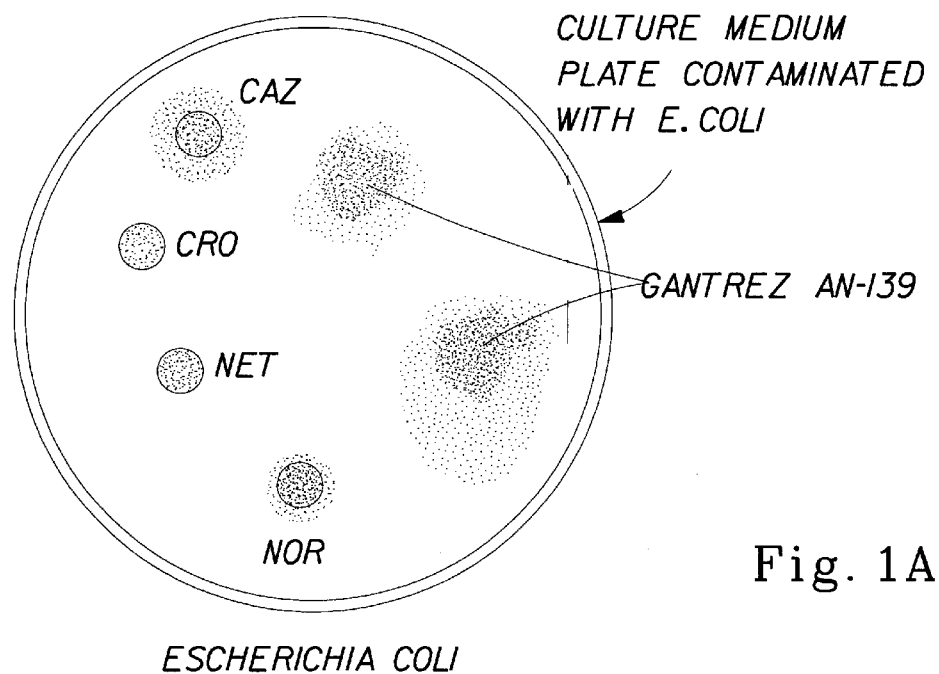
FIG. 1A shows a plan view of a culture plate after incubation showing the reaction of the applied reference antibiotics and the applied copolymer Gantrez AN-139 to *Escherichia Coli* bacteria.
Figure 1B:
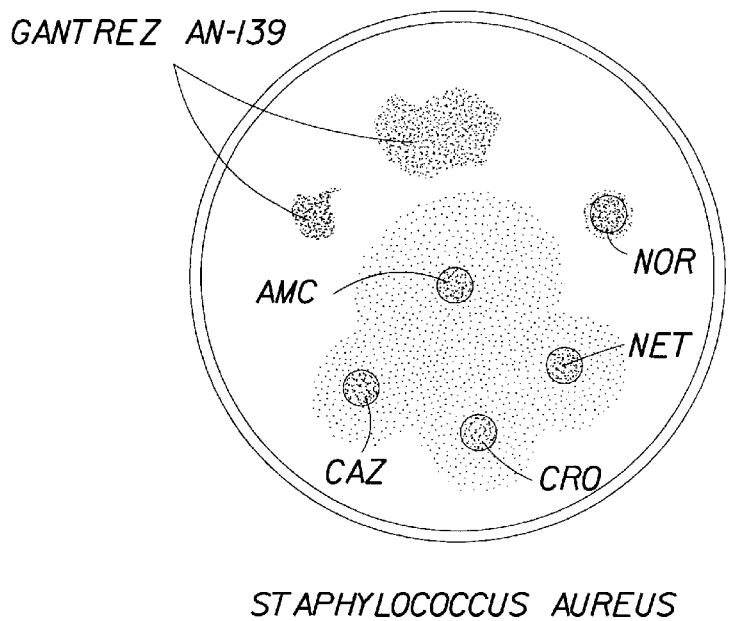
FIG. 1B shows a plan view of a culture plate after incubation showing the reaction of the applied reference antibiotics and the applied copolymer Gantrez AN-139 to *Staphilococcus Aureus* bacteria.
Figure 1C:
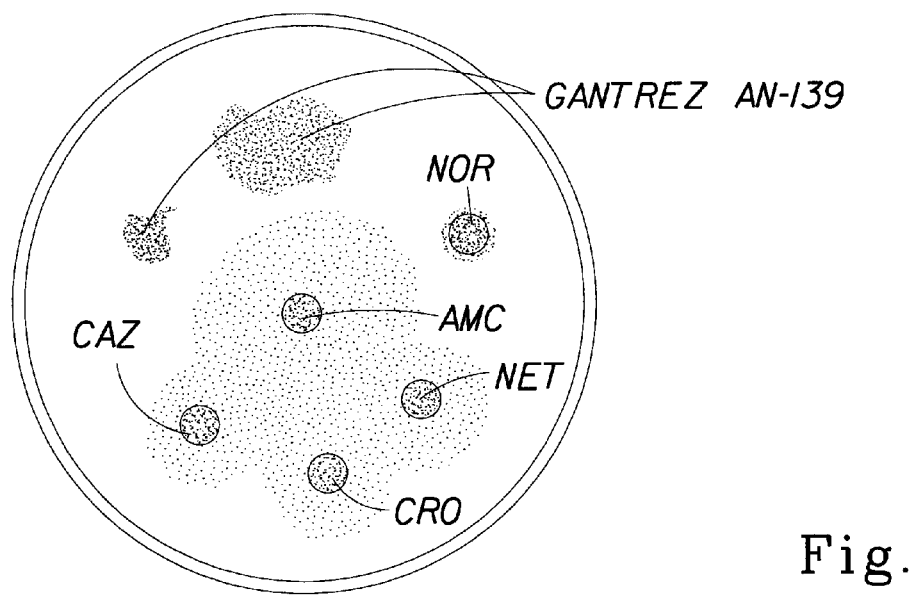
FIG. 1C shows a plan view of a culture plate after incubation showing the reaction of the applied reference antibiotics and the applied copolymer Gantrez AN-139 to Strepococcus bacteria.
Figure 1D:
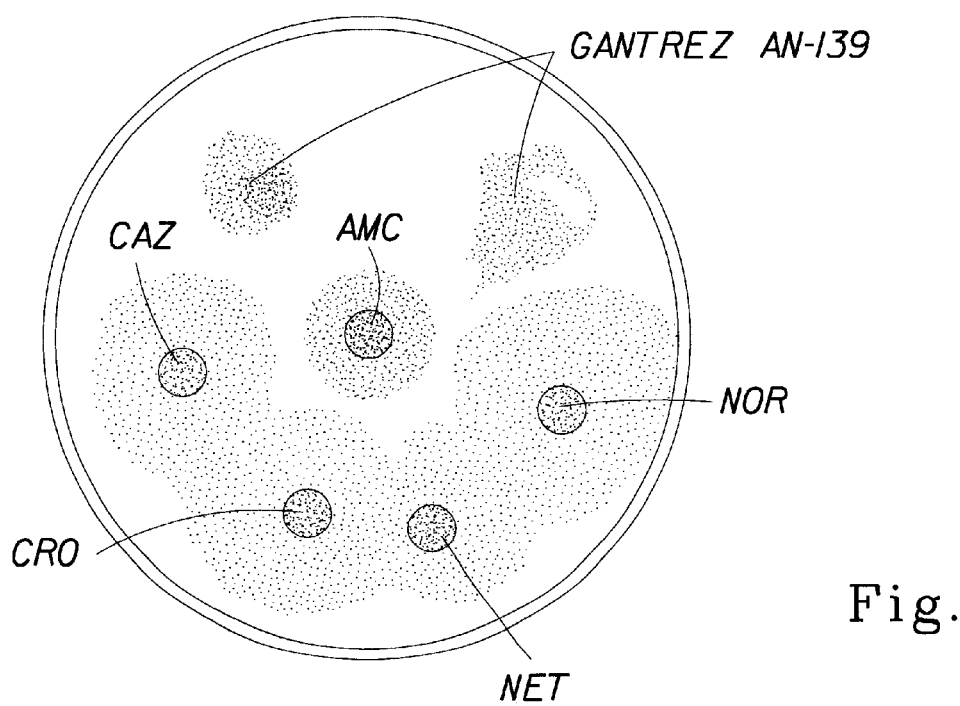
FIG. 1D shows a plan view of culture plate after incubation showing the reaction of the applied reference antibiotics and the applied copolymer Gantrez AN-139 to *Pseudomonas Aeruginosa* bacteria.

The test is carried out by putting a proper culture medium on a plate and suitably inoculating the surface of the culture medium with a bacterial stem/rod for examination. In the comparison plates, disks of absorbent paper soaked in reference antibiotics are placed on comparative culture plates. In the test plates, a copolymer according to the invention, such as, Gantrez AN-139, is applied in powdered form directly to a culture plate. The plates are maintained at a temperature of 37° C. for 24 hours, and the antibiotic or copolymer spreads in the culture medium and creates gradients of concentration around the disks in the case of the antibiotics or point of direct application in the case of Gantrez AN-139. The size of the inhibition around the antibiotic disks or point of application of Gantrez, illustrates the degree of sensitivity to the bacteria (see plates depicted in FIGS. 1A, 1B, 1C, 1D, and 1E) or to the fungus (see plate depicted in FIG. 1F).

FIGS. 1A, 1B, 1C, 1D 1E, and 1F show a series of culture medium plates contaminated all over their surface with *Escherichia Coli* (1A), *Staphilococcus Aureus* (1B), *Streptococcus* (1C), *Psedomonas Aeruginosa* (1D), *Proteus Vulgaris* (1E), and *Aspergillus Niger* (1F), respectively. Gantrez AN-139 is applied at two points directly to the surface of the culture medium as indicated in the representatives of the photos and the results show that the region of the culture medium to which the polymer is applied is sterile. These regions are distinguishable as they appear as transparent regions. Paper discs soaked in the reference antibiotics which are placed on the surface of the culture medium provide a direct comparison. Any inhibitory action by the antibiotic is seen as a transparent halo forming around the paper disk.

Similar results are observed when Gantrez AN-139 is applied directly to the surface of culture medium plates inoculated with *Escherichia Coli, Staphilococcus Aureus,* Streptococcus, *Psedomonas Aeruginosa, Proteus Vulgaris,* and *Aspergillus Niger* in the case of the plates indicated as FIGS. 1A, 1B, 1C, 1D, 1E and 1F, respectively.

The reference antibiotics tested are indicated in FIGS. 1A, 1B, 1C, 1D, 1E and 1F by the following abbreviations:
NOR: Norfloxacin 10 µg
NET: Netilmicin 30 µg
CRO; Ceftriaxone 30 µg
CAZ: Ceftazidime 30 µg
AMC: Amoxicillin+Clavulanic Acid 30 µg.

Gantrez AN-139 does not produce the inhibition rings represented as halos which can be seen for the test antibiotics, but Gantrez can be seen to cause the surface of the culture plates at the point to which it is applied to be completely sterile. The fact that Gantrez does not cause this halo around the point of application is not due to any difference in anti-bacterial or anti-mycotic activity, but can be attributed to the fact that the antibiotics have far lower molecular weights than the polymeric Gantrez, so that the solubility/molecular diffusibility of the antibiotics in the culture medium is far higher than that of Gantrez or any other copolymer according to the invention. It is observed that when Gantrez is incubated at a temperature of 37° C. for 24 hours after being placed on a culture medium previously seeded with a bacterial strain, the copolymer adsorbs water from the culture medium due to its hydrophilic character to form a transparent gel which is completely sterile.

The prolonged anti-bacterial action of Gantrez which has been observed may be useful for certain applications.

EXAMPLE 2

Microbiological Analysis to Verify the Anti-bacterial and Anti-mycotic Activity of test polymers Gantrez S-95, Stabileze QM and Gantrez MS-955.

Gantrez S-95 (copolymer of methyl vinyl ether/maleic acid), Stabileze QM (copolymer of methyl vinyl ether/maleic anhydride crosslinked with 1,9-decadiene) and Gantrez MS-955 (mixed sodium/calcium salt of the acid form of Gantrez) have anti-bacterial properties. A test culture medium surface covered with one of these test polymers, each according to the invention, is seen to be completely sterile (bacterial absence).

The test method used is the method of diffusion described in Example 1. The polymers of the invention do not produce inhibition rings which are seen in the comparison results with antibiotics but they do make the surface of the culture plate perfectly sterile.

Details of the method used to determine the anti-bacterial properties of the products under examination is as following: a sterile tampon is soaked in a broth Heart Brain (oxoide code PV 120 N) and after having picked up a colony of bacteria to test, the surface of a medium plate prepared with Mueller-Hinton Agar (Oxoide Code PS 120 A) is inoculated by means of streaking. The Mueller-Hinton Agar is mainly used in sensitivity tests of antibiotics and represents the standard for the Kirby-Bauer method (Bauer A. W, Kirby W. M., Sherris J:C: and Turk M. 1966 Amer J: Clin. Path. 45 493–496) and its quality characteristics are specified by the NCCLS (National Committee of Clinical Laboratory Standards 1984 Performance Standards for Antimicrobial Disk Susceptibility Tests).

On the same surface inoculated with Mueller-Hinton Agar, the polymers according to the invention are applied in powdered form directly to the agar surface. A comparative plate is prepared having a certain number of disks soaked in antibiotics. All plates are placed at 37° C. for 24 hours after which the results can be assessed.

The test copolymers according to the invention were applied over the entire surface of the Mueller Hinton Agar inoculated by bacteria selected from *Escherichia Coli, Proteus Mirabilis, Pseudomonas Mallei, Staphylococcus Aureus, Klebsiella Pneumoniae, Staphylococcus Epidermidis, Pseudomonas Aeruginosa* and *Salmonella Typhi*. After the test had been carried out, in each case the appearance of the agar is transparent and no growth of the bacteria was detected. The surface of the plate was in each case completely sterile.

A comparison test plate was prepared in the same manner each time a plate was prepared with a polymer according to the invention and the experimental conditions were identical. 8 paper disks each soaked in different antibiotics were spotted around the outer edge of the test plate. A transparent halo surrounding a disk represents a region of inhibition in bacterial growth.

The antibiotics tested were as follows:
AMC: Amoxicillin+Clavulanic Acid 30 µg
CAZ: Ceftazidime 30 µg
CRO: Ceftriaxone 30 µg
SXT: Sulfamethoxazol-Trimethoprim 25 µg
NET: Netilmicin 30 µg
NOR: Norfloxacin 10 µg
PRL: Piperacillin 100 µg
NA: Nalidixic Acid 30 µg Several runs of each experiment were carried out.

Figure 2:
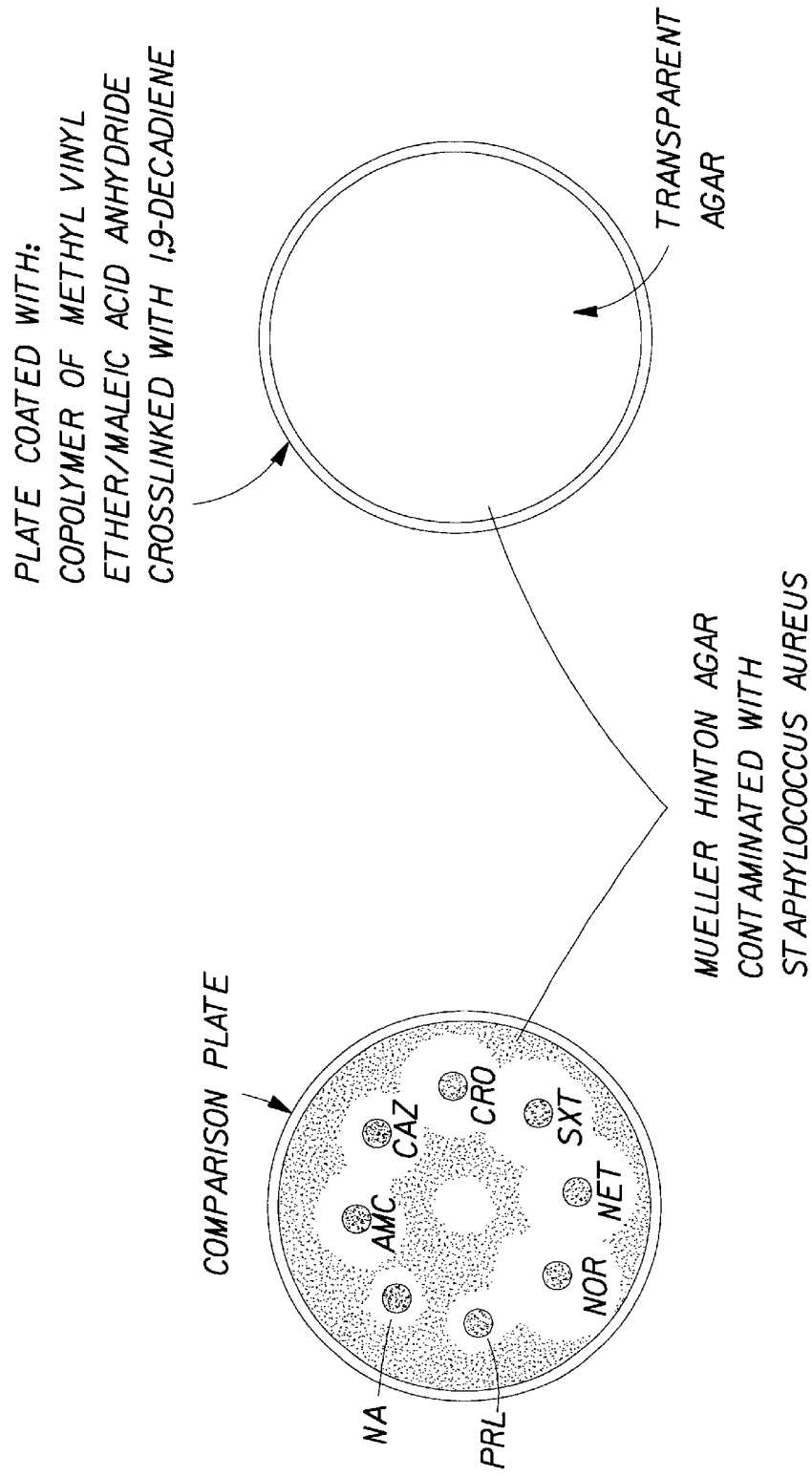
FIG. 2 shows a comparison of the plan view of two culture plates after incubation, showing the reactions of the applied reference antibiotics and the applied copolymers to the *Staphylococcus Aurelus* bacteria.

The copolymers of methyl vinyl ether/maleic acid, methyl vinyl ether/maleic anhydride copolymer crosslinked with 1,9-decadiene and the mixed sodium/calcium salt of the copolymer of methyl vinyl ether/maleic acid were all successful at inhibiting growth of each of the bacteria used across the whole surface of the culture medium. In the comparison plate, inhibition halos were seen around all of the antibiotic disks for each bacteria tested. The diameter of the halo was proportional to the effectiveness of the particular antibiotic against the bacteria tested. By way of further explanation FIG. 2 illustrates the results seen when the copolymer of methyl vinyl ether/maleic athydride crosslinked with 1,9-decadiene is tested on a plate contaminated with *Staphylococcus Aureus*. FIG. 2 also shows the comparison test plate.

It can be concluded that polymers of the invention under examination show good anti-bacterial activity to all of the microbes tested and also on those bacteria that have a considerable resistance to anti-bacterial action such as *Pseudomonas Aeruginosa*. When the polymer according to the invention is placed in contact with the culture medium inoculated with bacteria, the polymers are shown to sterilize the covered surface.

From the three products tested, the copolymer of methyl vinyl ether/maleic acid shows a greater anti-bacterial power.

These tests illustrate that the copolymers of the invention have high anti-microbial activity when tested against the aforementioned microorganisms when compared with the action of standard antibiotics such as amoxicillin/clavulanic acid, netilmicin and norfloxacin. The results show that the surface covered with the copolymer remains sterile for the duration of the test (48 hours) which is the same result seen for the reference antibiotics. The only difference noted is that in the case of the copolymers of the invention, the sterile area on the test surface coincides with the area of the copolymer. In the case of the antibiotics, however, sterile halos are seen around the area directly covered by the antibiotic. This is due to the different solubilities of the test copolymers and antibiotics in the culture medium, causing the antibiotics to diffuse out of the directly covered area.

EXAMPLE 3

Anti-mycotic Properties.

The copolymers of Example 2 according to the invention also demonstrate anti-mycotic activity. The anti-mycotic activity of the polymers was tested on *Candida Albicans* and *Aspergillus Niger*. The method used is the following: A sterile tampon is soaked in Broth Heart Brain and after having taken a colony of fungi, the surface of the medium plate, prepared with Sabouraud Dextrose Agar, is inoculated by streaking. The formulation of this medium corresponds to the changed proposal by Carlier (Carlier, Guendoline I. M. 1948 Brit J. Derm. Syph. 60, 61–63.) from the agar described by Sabouraud (Sabouraud R. 1910 "Les Teignes", Mason Paris) and it is suitable for the culture and the differentiation of fungi. The entire surface of the agar is coated directly with a polymer according to the invention which is applied in a powdered form.

By way of comparison, paper disks are soaked in various antibiotics and placed on the same inoculated Sabouraud Dextrose Agar surface. The antibiotics used in this example are the same as used in Example 2 with the exception of Nalidixic Acid (NA) which is substituted with Pipemidic Acid 20 ug (PIP). All test plates were placed at 37° C. for 24 hours after which readings were taken.

The products under examination have an excellent anti-mycotic action which is prolonged until the fifth day of observation with the plates remaining at 37° C. The results are shown in FIG. 3.

Figure 3:
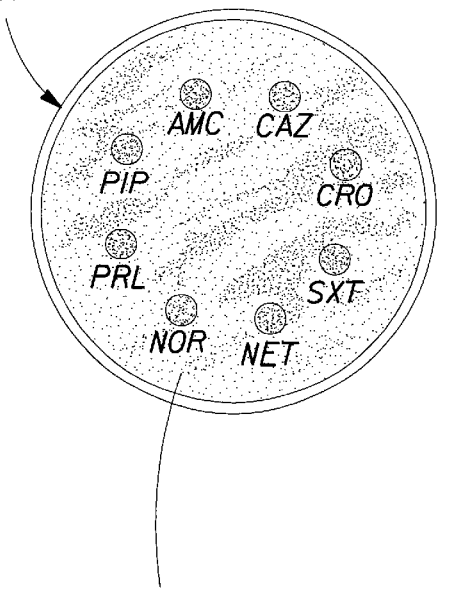
FIG. 3 shows a comparison of the plan view of two culture plates after incubation, showing the reactions of the applied reference antibiotics and the applied copolymers to the *Candida Albicans* bacteria and *Aspergillus Niger* fungus.
Figure 3:
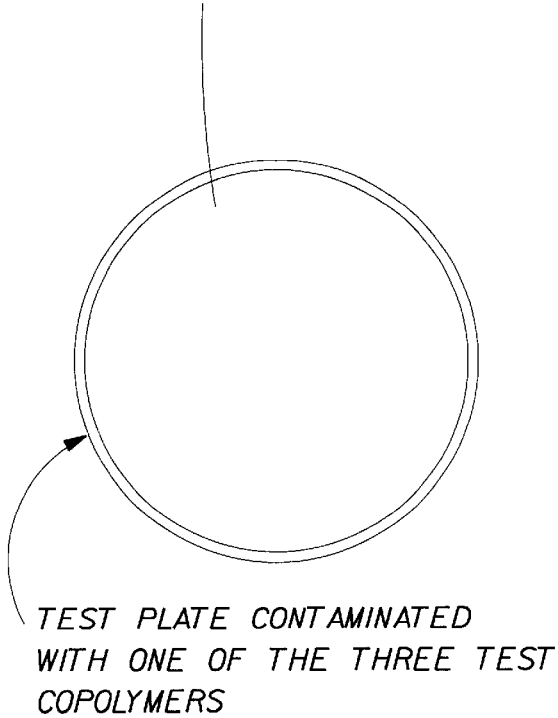

FIG. 3 shows that the comparison plates show no inhibition of fungal growth. No areas of fungal inhibition can be seen surrounding the antibiotic disks. In contrast the plates coated with a copolymer according to the invention demonstrate no fungal growth. When the copolymer according to the invention is used in contact with the culture medium inoculated with fungi, it can be seen that the copolymers of the invention are able to sterilize the covered surface. The methyl vinyl ether/maleic acid copolymer shows the greatest anti-mycotic power.

What is claimed is:

1. The method of controlling odor in a hygienic article comprising incorporating into said hygienic article a copolymer comprising at least two different ethylenically unsaturated monomers A and B or a derivative of said copolymer wherein monomer A is according to the formula:

$$R^1-CH=CH-R^2$$

and wherein monomer B is according to the formula:

$$R^3-C(R^1)=C(R^2)-R^4$$

wherein $R^1$ and $R^2$ are independently selected from hydrogen; hydroxy; halogen; carboxy; sulfo; phenyl; phenoxy; $C_{1-6}$ alkyl, $C_{1-6}$ alkoxy; $C_{1-6}$ aminoalkyl; $C_{1-6}$ haloalkyl; $C_{1-6}$ alkylphenyl; amino and $C_{1-6}$ alkylamino, $R^3$ is an acidic group or a derivative thereof and $R^4$ is a group selected from any of the groups given hereinbefore for $R^1$, $R^2$ or $R^3$, with the proviso that neither monomer A nor monomer B is an ester having a quaternary ammonium compound.

2. The method according to claim 1 wherein $R^3$ is a sulfo or carboxy group or a derivative thereof.

3. The method according to claim 1 or claim 2 wherein $R^4$ is an acidic group, preferably a sulfo or carboxy group, or a derivative thereof.

4. The method according to claim 1 wherein $R^1$ and $R^2$ in monomer B are both hydrogen.

5. The method according to claim 1 wherein monomer A is $C_{1-6}$ alkyl vinyl ether.

6. The method according to claim 1 wherein monomer A is methyl vinyl ether and monomer B is maleic acid or maleic anhydride.

7. The method according to claim 1 wherein said copolymer comprises a molar content of monomers A and B in a ratio of from 60:40 to 40:60.

8. The method according to claim 1 wherein monomers A and B form a substantially alternate copolymer.

9. The method according to claim 1 wherein said copolymer has a molecular weight of about 10,000 Daltons or more.

10. The method according to claim 1 wherein derivatives of said copolymer are selected from free acidic forms of said copolymer; esterified forms of said copolymer; amide derivatives or imide derivatives of said copolymer and mixtures of said amide and imide derivatives thereof; complexes between said copolymer and poly-vinyl pyrrolidone; complexes between said copolymer and iodine; derivatives of said copolymer with polyhydroxy compounds and polyamines; derivatives of said copolymers with glycerin, glycol, polyglycol and polyvinyl alcohol and salts of said copolymer, preferably salts derived from alkaline metals, earth alkaline metals, aluminium, iron, zinc, silver, copper, mercury and mixed salts thereof.

11. The method according to claim 1 wherein the copolymer is incorporated into the hygienic article as an adhesive.

12. The method according to claim 1 wherein the copolymer is incorporated into the hygienic article as a coating.

13. The method according to claim 1 wherein the hygienic article is a disposable absorbent article.

14. The method according to claim 13 wherein the disposable absorbent article is a tampon or a pantiliner.

15. The method according to claim 1 wherein the copolymer is incorporated into non-woven or woven components of the hygienic article.

16. The method according to claim 13 wherein the copolymer is incorporated into non-woven or woven components of the hygeinic article.

17. The method according to claim 1 wherein the copolymer is incorporated into the hygienic article as a portion which will contact an area of a body.

18. The method according to claim 13 wherein the copolymer is incorporated into the hygienic article as a portion which will contact an area of a body.

* * * * *